United States Patent
Sata

(12) United States Patent (10) Patent No.: US 6,267,941 B1
(45) Date of Patent: *Jul. 31, 2001

(54) CATALYST SYSTEM FOR DEODORIZATION OF A MIXTURE OF SULFUR COMPOUNDS AND COMPOUNDS SUCH AS ALDEHYDES, ALCOHOLS AND/OR HYDROCARBONS

(75) Inventor: Naoaki Sata, Tokyo (JP)

(73) Assignee: NEC Corporation, Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/998,467

(22) Filed: Dec. 26, 1997

(30) Foreign Application Priority Data

Jan. 8, 1997 (JP) .................................................. 9-001385

(51) Int. Cl.$^7$ .................................................. B01J 8/00
(52) U.S. Cl. .................. 423/244.1; 423/244.01; 423/244.02; 423/244.09; 423/213.2; 423/213.5; 502/312; 502/313; 502/314; 502/315; 502/316; 502/318; 502/319; 502/324; 502/326; 502/331; 502/337; 502/338; 502/339; 502/345; 502/353
(58) Field of Search .................. 423/244.01, 239.1, 423/213.5, 240 S, 213.2, 242.1, 244.09, 244.1, 244.02; 502/326, 313, 324, 314, 332, 317, 330, 517, 312, 315, 316, 318, 319, 331, 337–339, 345, 353; 208/208 R; 422/120, 122, 123, 169, 188, 189, 190

(56) References Cited

U.S. PATENT DOCUMENTS

| | | | |
|---|---|---|---|
| 690,133 | * 12/1901 | Clemm et al. | 423/242.1 |
| 4,251,347 | * 2/1981 | Rausch et al. | 208/57 |
| 4,446,005 | * 5/1984 | Eberly, Jr. et al. | 208/91 |
| 4,449,991 | * 5/1984 | Brannon et al. | 55/73 |
| 4,690,806 | * 9/1987 | Schorfheide | 423/230 |
| 5,266,543 | * 11/1993 | Matsumoto et al. | 502/66 |
| 5,474,670 | * 12/1995 | Daage et al. | 208/210 |
| 5,687,565 | * 11/1997 | Modica et al. | 60/274 |

FOREIGN PATENT DOCUMENTS

| | | | |
|---|---|---|---|
| 56-141853 | * 11/1981 | (JP) . | |
| 60-031824 | * 2/1985 | (JP) . | |
| 0631128 | 2/1994 | (JP) | B01D/53/02 |
| 7-284670 | 10/1995 | (JP) | B01J/29/16 |
| 8-047645 | 2/1996 | (JP) | B01J/29/072 |

* cited by examiner

*Primary Examiner*—Tom Dunn
*Assistant Examiner*—Cam N. Nguyen
(74) *Attorney, Agent, or Firm*—Hayes, Soloway, Hennessey, Grossman & Hage, PC

(57) ABSTRACT

A catalyst system for deodorization and an apparatus for deodorization, each of which comprises a pretreating catalyst and a noble metal catalyst, the pretreating catalyst converting a sulfur atom of low oxidation state which deactivates the noble metal catalyst into a sulfur atom of high oxidation state which has little deactivation effects thereon, the noble metal catalyst oxidizing aldehyde, etc., wherein a material to be deodorized is brought into contact with the pretreating catalyst prior to being brought into contact with the noble metal catalyst. As the pretreating catalyst, a catalyst comprising at least one selected from the group consisting of vanadium, chromium, manganese, iron, cobalt, nickel, copper and oxides thereof is used, while as the noble metal catalyst, a catalyst comprising at least one selected from the group consisting of ruthenium, rhodium, palladium, silver, rhenium, osmium, iridium, platinum and gold is used. According to the catalyst system, a striking deodorizing-effect is provided to, in particular, a mixture of sulfur cop s of low oxidation state and compounds such as aldehydes or alcohols.

8 Claims, 1 Drawing Sheet

CATALYST SYSTEM FOR DEODORIZATION OF A MIXTURE OF SULFUR COMPOUNDS AND COMPOUNDS SUCH AS ALDEHYDES, ALCOHOLS AND/OR HYDROCARBONS

BACKGROUND OF THE INVENTION

1. FIELD OF THE INVENTION

The present invention relates to a catalyst for deodorization and a deodorizing apparatus using the catalyst and in particular, relates to a catalyst for deodorization which provides an excellent deodorization effect to a mixture of sulfur compounds and compounds such as aldehydes, alcohols or hydrocarbon compounds, and an apparatus for deodorization using the same.

2. PRIOR ART

Hitherto, noble metal catalysts in which platinum, palladium, or both platinum and palladium are supported on a suitable support have been used as a catalyst for deodorization. These catalysts promote a reaction wherein a gas to be deodorized is oxidized and decomposed by oxygen in air so as to provide a deodorization effect, which are, in particular, effective on aldehydes, alcohols and hydrocarbon compounds.

However, These catalyst are deactivated by materials to be deodorized which contain sulfur compounds of low oxidation state such as dimethyl sulfide or methanethiol. Therefore, when such materials to be deodorized are present, it is difficult to use these catalysts as the deodorization catalyst.

In case of materials to be deodorized which contain sulfur compounds, catalysts having an oxide of cobalt, manganese, etc. as an active component, which have relatively strong resistance against such materials are used. For example, Japanese Patent KOKAI(Laid-Open) No.31128/94 discloses a deodorant which comprises an oxide of cobalt and/or manganese, and zeolite. Furthermore, in Japanese Patent KOKAI Nos.47645/96 and 284670/95, a catalyst containing an activated manganese dioxide, a copper-supporting zeolite and copper oxide as an effective component is used so as to attempt a deodorization thereby. However, all of such catalysts provide some effects on the sulfur compounds, while insufficient or no effects on aldehydes, alcohols and the like.

On the other hand, gases, which are emitted from crude waste disposal machines, contain aldehydes, amines, alcohols and the like as well as we sulfur compounds, and therefore, it was impossible to treat such gases, with the conventional cataysts mentioned above.

SUMMARY OF THE INVENTION

It is, because a sulfur atom of dimethylsulfide or the like strongly adsorbs on active sites of the noble metal catalysts mentioned above, that these catalysts are deactivated by dimethylsulfide or the like. It has been found that the effect that the catalyst is deactivated by such an adsorption is remarkable in compounds which have a sulfur atom of low oxidation state, while such effect is little observed in a sulfur compound of high oxidation state. The present inventor has been found that prolongation of life of a noble metal catalyst and a high-efficient oxidative decomposition are achieved by using a combination of a noble metal catalyst and a catalyst which oxidizes compounds having a sulfur atom of low oxidation state such as dimethylsulfide to a high oxidation state such as sulfons.

It is an object of the present invention to provide a catalyst system which has an effective deodorization effect on materials to be deodorized which contain compounds such as aldehydes, alcohols, amines or hydrocarbon compounds, as well as sulfur compounds of low oxidation state.

It is another object of the present invention to provide an apparatus in which a catalyst system is arranged so that the catalyst system has an effective deodorization effect on materials to be deodorized which contain compounds such as aldehydes, alcohols, amines or hydrocarbon compounds, as well as sulfur compounds of low oxidation state.

According to one aspect of the present there is provided a catalyst system for deodorization which comprises a pretreating catalyst and a noble metal catalyst, the pretreating catalyst being a catalyst for converting a sulfur compound of low oxidation state which is included in materials to be deodorized into a sulfur compound of high oxidation state, wherein the materials to be deodorized are brought into contact with the pretreating catalyst prior to being brought into contact with the noble metal catalyst.

According to another aspect of the present invention, there is provided an apparatus for deodorization which is provided with a catalyst tower inside which the pretreating catalyst is positioned upstream of channels for a gas to be deodorized, and the noble metal catalyst is positioned downstream of the channels, wherein the pretreating catalyst is the one for converting the sulfur compound of low oxidation state which is included in the gas to be deodorized into a sulfur compound of high oxidation state.

Furthermore, the catalyst system for deodorization of the present invention is characterized by comprising a pretreating catalyst and a noble metal catalyst, the pretreating catalyst comprising at least one selected from the group consisting of vanadium, chromium, manganese, iron, cobalt, nickel, copper and oxides thereof, and the noble metal catalyst comprising at least one selected from the group consisting of ruthenium, rhodium, palladium, silver, rhenium, osmium, iridium, platinum and gold.

In particular, the catalyst system for deodorization of the present invention preferably comprises a pretreating catalyst which contains manganese oxide(IV) and/or vanadium oxide(V), and a noble metal catalyst which contains palladium and/or platinum.

Further another aspect of the present invention relates to a use of a catalyst system which comprises a noble metal catalyst and a pretreating catalyst for deodorizing a malodorous gas containing materials which provides a deactivation effect on the noble metal catalyst, wherein the use comprises the steps of: bringing the gas to be deodorized which contains materials which provides the deactivation effect on the noble metal catalyst into contact with the pretreating catalyst prior to bringing the gas into contact with the noble metal catalyst so as to convert the gas into other materials having less deactivation effect; and then, bringing the gas into contact with the noble metal catalyst.

PREFFERED MODES OF EMBODIMENT

Figure 1:
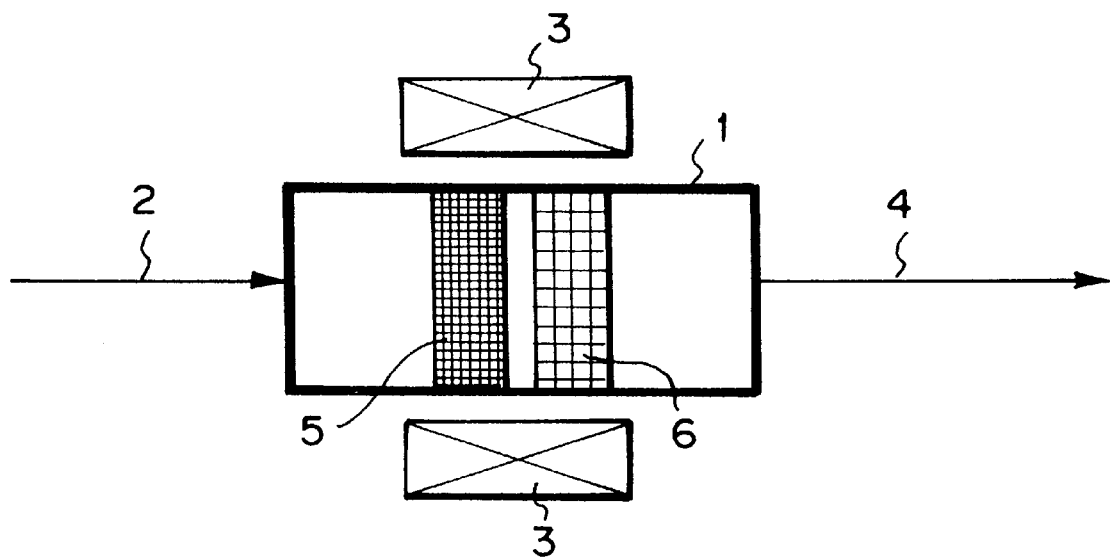
FIG. 1 is an explanation drawing which illustrates an example of the apparatus for deodorization of the present invention.

As the pretreating catalyst in the present invention, a catalyst which comprises at least one selected from the group consisting of vanadium, chromium, manganese, iron, cobalt, nickel, copper, and oxides thereof is suitably used. The pretreating catalyst is constituted by an oxidation catalyst which has relatively strong resistance against compounds having a sulfur atom of low oxidation state, which is used to oxidize compounds containing a sulfur atom of low oxidation state such as disulfides to materials of high oxidation state such as sulfones. At this time, it is necessary to control the oxidation power thereof so that the compound can be requisitely and sufficiently oxidized to sulfone. According to the catalyst for deodorization of the present invention, the metals and their oxides which are included in the above group can be suitably selected or combined together depending upon the composition of a gas to be deodorized so as to control the oxidation power thereof. It is effective to use manganese oxide(IV) and/or vanadium oxide(V), in particular, when the pretreating catalyst comprising manganese oxide(IV) and 5 to 20% by weight of vanadium oxide(V) (the whole catalyst is represented as 100% by weight) is used, a catalyst which is effective on many gases to be deodorized can be realized. A manganese oxide(IV)-vanadium oxide(V) catalyst can be prepared according to various methods, for example, as follows. Namely, manganese oxide(IV) which is obtained by decomposing potassium permanganate with nitric acid and vanadium oxide(V) which is obtained by decomposing amnonium metavanadate at a temperature of 500° C. in an air flow are mixed in desired amounts, and said mixture is fired at a temperature of 200° C. in an oxygen flow so as to obtain a manganese oxide(IV)-vanadium oxide(V) catalyst of the present invention. Incidentally, a support is not necessary for this catalyst except under special occasions. Furthermore, depending upon the use of the catalyst, the form of an apparatus, the flow rate of a gas to be deodorized or the like, the shape of the catalyst may be suitably selected from tablets, fine particles, honeycombs and the like.

The noble metal catalyst is used to oxidize aldehydes, alcohols, amines and hydrocarbon compounds, which is preferably selected from the group consisting of ruthenium, rhodium, palladium, silver, rhenium, osmium, iridium, platinum and gold. Then the compounds having sulfur atoms of low oxidation state which causes the deactivation of the noble metal catalyst are oxidized by the pretreating catalyst so as to be converted into c s having sulfur atoms of high oxidation state such as sulfones which have little deactivation effects.

Therefore the prolongation of life of the noble metal catalyst and a high-efficient oxidative decomposition can be achieved. The noble metal catalyst can be suitably selected from metals which are contained in the group mentioned above, or can be obtained by a combination of said metals so as to increase deodorization efficiency. In particular, it has been confirmed that a catalyst which is effective to many different kinds of gases to be deodorized is realized by using platinum or gold. Furthermore, although a support for the noble metal catalyst is not particularly limited, for example, γ-alumina or the like can be used.

Thus, as a catalyst system for deodorization is in combination of a pretreating catalyst to oxidize compounds containing sulfur atoms of low oxidation state into sulfones, and a noble metal catalyst to oxidize aldehydes into carbon dioxide and water, the prolongation of life of the noble metal catalyst and a high-efficient oxidative decomposition can be achieved, wherein as the use mode of the catalyst for deodorization of the present invention, the pretreating catalyst is desirably positioned upstream of channels for a gas to be deodorized, and the noble metal catalyst is desirably positioned downstream of the channels, because the compounds including sulfur atoms of low oxidation state can be effectively converted into sulfones by such an arrangement.

The catalyst system for deodorization of the present invention is effective on aldehydes, alcohols, amines, and hydrocarbon compounds, and furthermore effective on compounds which contain a sulfur atom of low oxidation state such as sulfides, disulfides or alkylthiols. In particular, an catalyst is effective on a mixture of the aldehyde compound and a sulfur compound.

The apparatus for deodorization of the present invention is characterized in that the pretreating catalyst and the pecious metal catalyst as mentioned above are arranged in series inside a catalytic reaction tower, wherein the pretreating catalyst is positioned upsteam of channels for a gas to be deodorized, while the precious metal catalyst is positioned downsteam of the channels. If such conditions are satisfied, the form of a general catalytic reaction tower which has been used hitherto can be used as it is. As shown in FIG. 1, pretreating catalyst bed(5) is positioned upstream of gas to be deodorized(2) as shown by arrows, while noble metal catalyst bed(6) is a positioned downstream thereof, wherein the catalyst beds (5) and (6) are properly spaced, provided that both catalysts are not mixed with each other, and a space between the catalyst beds(5) and (6) is not specifically limited. Heater(3) is positioned in the jacket of reaction tower(1). After treatment, deodorized gas(4) is removed.

Figure 2:
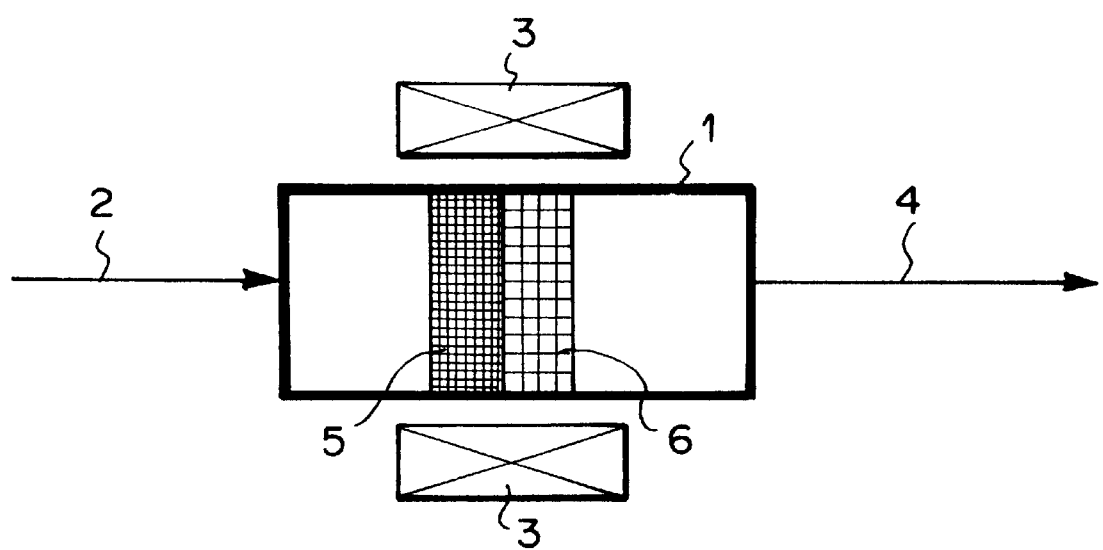
FIG. 2 is an explanation drawing which illustrates another example of the apparatus for deodorization of the present invention.

Furthermore, as shown in FIG. 2, the pretreating catalyst bed(5) and the noble metal catalyst bed(6) can be arranged by bringing both catalyst beds(5) and (6) into contact with each other not to be mixed with each other. When a pellet-shaped catalyst is used, the boundary of both catalyst beds is preferably divided by, for example, a wire netting. On the other hand, when at least one of both catalysts is a monolithic catalyst, for example, a catalyst which was formed in the shape of a honeycomb,a divider therebetween is unnecessary because there is no possibility of both catalysts to be mixed with each other. Incidentally, the shape of the catalyst tower (1) does not specifically matter. Such a structure of the catalytic reaction tower can provide effective treatments of compounds including sulfur of low oxidation state which deactivate the noble metal catalyst, and furthermore can achieve the high efficiency of the catalyst and the prolongation of the life thereof.

Conditions for deodorizing the gas by using the catalyst for deodorization of the present invention are suitably selected according to the kind of the gas to be deodorized; for example, preferably the reaction temperature is in the range of 200° C. to 400° C. and the space velocity (SV) is in the range of about 1000 to 10000 h$^{-1}$. Furthermore, a contact system for bringing the gas to be deodorized into contact with the catalyst is preferably a fixed bed, while the contact system in which a fluidized bed or a moving bed is employed can be also used under such conditions that the pretreating catalyst and the noble metal catalyst are not mixed with each other.

EXAMPLES

Hereinafter, the present invention will be more specifically explained by the following examples.

EXAMPLE 1

A catalyst system for deodorization of the present invention which comprises a pretreating catalyst and a noble metal catalyst was used, wherein the pretreating catalyst comprises manganese oxide(IV) and vanadium oxide(V) in an amount of 5% by weight (in which all of said catalysts was represented as 100% by weight), and the noble metal catalyst comprises a platinum supporting alumina catalyst in which 1% of platinum is supported; and an apparatus for deodorization of the present invention is shown in FIG. 1, wherein a silica tube(having an inner diameter of 16 mm and a length of 500 mm) as catalyst tower (1), pretreating catalyst bed(5) and noble metal catalyst bed(6) are provided, wherein the silica tube was filled with the pretreating catalyst bed(5) having a volume of 10cm$^3$ and the noble metal catalyst bed(6) having a volume of 5 cm$^3$, the pretreating catalyst bed(5) and the noble metal catalyst bed(6) being spaced about 2cm apart; and thereby a simulated malodorous air including 10ppm of dimethylsulfide and ethanal(acetaldehyde) having the same concentration was treated at a temperature of 300° C. under the condition of SV/h$^{-1}$=30000. 96% of Dimethylsulfide and 100% of ethanal were oxidized and removed, respectively. Although the treatment was carried on for a period of 100 hours, no deterioration in activation was observed.

Comparative Example 1

A treatment was carried out under the same conditions as that in Example 1except that only the platinum-supporting alumina catalyst in which 1% of platinum is supported was used instead of the catalyst system for deodorization of the present invention. In the early stage of reaction, the removal ratio of dimethylsulfide was 34%, while that of ethanal was 63%. According to measurements after the simulated malodorous air was passed through for a period of 100 hours, the removal ratio of dimethylsulfide was 2%, while that of ethanal was 9%.

Example 2

The same apparatus for deodorization as that used in Example 1was filled with a catalyst system for deodorization of the present invention which comprises a pretreating catalyst and a noble metal catalyst, wherein the pretreating catalyst comprises manganese oxide( IV) and vanadium oxide(V) in an amount of 20% by weight, the noble metal catalyst comprises a platinum-palladium supporting alumina catalyst in which platinum and palladium were supported by 1.5%, respectively; and then a simulated malodorous air which includes 100 ppm of methanal(formaldehyde), trimethylamine in an amount of the same concentration, and 10 ppm of methanethiol was treated at a temperature of 300° C. under the condition of SV/h$^{-1}$=30000. 99% of Methanal, 94% of trimethylamine and 97% of Methanethiol were oxidized and removed. Although the treatment was carried on for a period of 100 hours, no deterioration in activation was observed.

Example 3

The same apparatus for deodorization as that in Example 1 was filled with a catalyst system for deodorization of the present invention which comprises a pretreating catalyst and a noble metal catalyst, wherein the pretreating catalyst comprises manganese oxide(IV) and vanadium oxide(V) in an amount of 5% by weight, the noble metal catalyst comprises a palladium-supporting alumina catalyst in which 1.5% of palladium was supported; and then a simulated malodorous air which includes 330 ppm of acetic acid and 480 ppm of ethanal was treated at a temperature of 380° C. under the condition of SV/h$^{-1}$=10000. Both acetic acid and ethanal were removed by 100%, respectively.

Comparative Example 2

When a treatment was carried out under the same conditions as that in Example 3 except that only manganese oxide(IV) containing 5% by weight of vanadium oxide(V) was used instead of the catalyst system of the present invention, the removal ratio of acetic acid was 61%, while that of ethanal was 48%. Furthermore, when the treatment was carried out under the same conditions as that in Example 3 except that only a palladium-supporting alumina catalyst in which 1.5% of palladium was supported was used instead of the catalyst system of the present invention, the removal ratio of acetic acid was 68% while that of ethanal was 78%. From these results, assuming that there is no synergistic effect of both catalysts, the removal ratio of acetic acid comes to about 88%, while that of ethanal comes to about 89%. On the other hand, since according to the catalyst system of the present invention, the removal ratios of acetic acid and ethanal are 100%, respectively, it is clear that a catalyst system of the present invention provides more excellent effects as compared with a mere combination of the effect of each individual catalyst, which shows that a material which provides a deactivation effect to the noble metal catalyst is converted into another material, thereby the deodorization efficiency of the noble metal catalyst is strikingly improved.

Example 4

The same apparatus for deodorization as that in Example 1 was filled with the catalyst system for deodorization the present invention which comprises a pretreating catalyst and a noble metal catalyst, wherein the pretreating catalyst comprises manganese oxide(IV), 1% by weight of nickel oxide(II), and 5% by weight of vanadium oxide(V), the noble metal catalyst comprises a platinum-ruthenium supporting alumina catalyst in which platinum and ruthenium were supported by 2%, respectively; and then a simulated malodorous air which includes 100ppm of dimethylsulfide, 100ppm of methanethiol, 100ppm of limonene and 100ppm of ethanal was treated at a temperature of 400° C. under the condition of SV/h$^{-1}$ =10000. 98% of Dimethylsulfide, 93% of methanethiol, 99% of limonene and 99% of ethanal were treated, respectively.

Although this treatment was carried on for a period of 100 hours, no deterioration in activation was observed.

Example 5

The same simulated malodorous air as that in Example 4 was treated under the same conditions as those in Example 4 except that the catalyst system for deodorization of the present invention which comprises a pretreating catalyst and a noble metal catalyst was used, wherein the pretreating catalyst comprises manganese oxide(IV), 1% by weight of nickel oxide(II), and 10% by weight of vanadium oxide(V), the noble metal catalyst comprises a rhodium-palladium supporting alumina catalyst in which rhodium and palladium were supported by 1% by weight, respectively. 95% of Dimethylsulfide, 96% of methanethiol, 100% of limonene and 96% of ethanal were treated, respectively. Although this treatment was carried on for a period of 100 hours, no deterioration in activation was observed.

Example 6

The same simulated malodorous air as that in Example 5 was treated under the same conditions as those in Example 5 except that manganese oxide(IV) and 5% by weight of vanadium oxide(V) are used as the pretreating catalyst. 96% of Dimethylsulfide, 97% of methanethiol, 98% of limonene and 97% of ethanal were treated, respectively. Although this treatment was carried on for a period of 100 hours, no deterioration in activation was observed.

As mentioned above, the catalyst system for deodorization of the present invention can effectively decompose and/or deodorize a gas to be deodorized which includes aldehydes, sulfur compounds of low oxidation state, or other compounds. Furthermore, it is also possible to preponderantly remove a material to be removed with top priority by suitably selecting the catalyst.

Effects of the Invention

As mentioned above, according to the present invention, a pretreating catalyst and a noble metal catalyst are used, and a gas to be deodorized is brought into contact with the pretreating catalyst prior to being brought into contact with the noble metal catalyst, wherein the pretreating catalyst can convert a sulfur atom of low oxidation state by which the noble metal catalyst is deactivated, into a sulfur atom of high oxidation state which has little deactivation effects, and the noble metal catalyst can oxidize aldehydes; and thereby the catalyst system for deodorization which exhibits a high rate of deodorization of a mixture of compounds such as aldehydes and sulfur compounds, and has high resistance against the same, is provided.

on the other hand, in the apparatus for deodorization of the present inventions a pretreating catalyst is positioned upstream of the channels of a gas to be deodorized, while a noble metal catalyst is positioned downstream thereof, and therefore, compounds containing a sulfur atom of low oxidation state have been effectively converted into sulfur compounds of high oxidation state such as sulfones through the pretreating catalyst, and thereafter the deodorization treatment is carried out through the noble metal catalyst, and thereby the prolongation of life of the noble metal catalyst and a high-efficient oxidative decomposition can be realized.

What is claimed is:

1. A method for deodorization of a gas stream of waste materials including malodorous sulfur-containing compounds of low oxidation state mixed with air and one or more aldehydes, alcohols and/or hydrocarbon compounds, comprising the steps in sequence of (1) bringing said gas stream to be deodorized into contact with a pretreating catalyst comprising an oxide of a metal selected from the group consisting of vanadium, chromium, manganese, iron, cobalt, nickel, copper and a mixture thereof, whereby to convert the malodorous sulfur compounds of low oxidation state which are contained in said gas stream into non-malodorous sulfur compounds of high oxidation state, and (2) bringing the gas from step (1) into contact with a noble metal catalyst.

2. A method according to claim 1 wherein said nobles metal catalyst comprises at least one metal selected from the group consisting of ruthenium, rhodium, palladium, silver, rhenium, osmium, iridium, platinum and gold.

3. A method according to claim 1, wherein said sulfur-containing compounds of low oxidation state are selected from the group consisting of a sulfide, a disulfide, an alkylthiols and a mixture of one or more thereof, and said sulfur compounds of higher oxidation state are sulfones.

4. A method according to claim 1, wherein said pretreating catalyst comprises a mixture of manganese oxide (IV) and vanadium oxide (V).

5. A method according to claim 1, wherein said pretreating catalyst comprises a mixture of manganese oxide (IV), nickel oxide (II) and vanadium oxide (V).

6. A method according to claim 1, wherein said pretreating catalyst and/or said noble metal catalyst are formed in the shape of a honeycomb.

7. A method according to claim 1, wherein said pretreating catalyst and said noble metal catalyst are positioned in series within a catalyst reaction tower, spaced from one another.

8. A method according to claim 1, wherein said pretreating catalyst and/or said noble metal catalyst are formed in the shape of a honeycomb, and are in contact with each other.

* * * * *

UNITED STATES PATENT AND TRADEMARK OFFICE
CERTIFICATE OF CORRECTION

PATENT NO.    : 6,267,941 B1                                  Page 1 of 1
DATED         : July 31, 2001
INVENTOR(S)   : Naoaki Sata It is certified that error appears in the above-identified patent and that said Letters Patent is hereby corrected as shown below:

<u>Column 8,</u>
Line 11, insert "," after -- 1 --
Line 19, "alkylthiols" should be -- alkylthiol --

Signed and Sealed this

Eleventh Day of June, 2002

*Attest:*

*Attesting Officer*

JAMES E. ROGAN
*Director of the United States Patent and Trademark Office*